(12) United States Patent
Patel et al.

(10) Patent No.: US 7,868,173 B2
(45) Date of Patent: Jan. 11, 2011

(54) PRODRUGS OF BENZOQUINOLIZINE-2-CARBOXYLIC ACID

(75) Inventors: Mahesh Vithalbhai Patel, Aurangabad (IN); Vijaya Narayan Desai, Aurangabad (IN); Prasad Keshav Deshpande, Aurangabad (IN); Ravindra Dattatraya Yeole, Aurangabad (IN); Rajesh Prabhakar Kale, Amravati (IN)

(73) Assignee: Wockhardt Limited (IN)

( * ) Notice: Subject to any disclaimer, the term of this patent is extended or adjusted under 35 U.S.C. 154(b) by 976 days.

(21) Appl. No.: 11/715,921

(22) Filed: Mar. 9, 2007

(65) Prior Publication Data

US 2007/0219227 A1 Sep. 20, 2007

Related U.S. Application Data

(63) Continuation-in-part of application No. 11/430,017, filed on May 9, 2006, now abandoned.

(30) Foreign Application Priority Data

Mar. 7, 2006 (IN) .................. 321/MUM/2006

(51) Int. Cl.
*C07D 221/06* (2006.01)
*A61K 31/473* (2006.01)

(52) U.S. Cl. ............................. 546/98; 514/290; 546/79

(58) Field of Classification Search ................. 546/79, 546/98; 514/290
See application file for complete search history.

(56) References Cited

FOREIGN PATENT DOCUMENTS

| WO | 0068229 | * 11/2000 |
|----|---------|-----------|
| WO | WO0209758 A2 | 2/2002 |

OTHER PUBLICATIONS

Berge et al, 1977, Pharmaceutical Salts.*
Cabri Walter, et al, 2007 Polymorphism and Patent Market and Legal battles.*
Berge et al., Pharmaceutical salts. Review article. J Pharm Sci. Jan. 1977;66(1):1-19. (Abstract).

* cited by examiner

*Primary Examiner*—Rita J Desai
(74) *Attorney, Agent, or Firm*—Bio Intellectual Property Services (Bio IPS) LLC; O. M. (Sam) Zaghmout

(57) ABSTRACT

The instant invention relates to novel prodrugs of optically pure benzoquinolizine-2-carboxylic acid and pharmaceutical compositions that include the prodrugs. In particular, the present invention relates to the sulfonic acid salts of L-alanine and L-valine prodrugs of S-(−)-9-fluoro-6,7-dihydro-8-(4-hydroxypiperidin-1-yl)-5-methyl-1-oxo-1H,5H-benzo[i,j]quinolizine-2-carboxylic acid. The compounds and compositions of the invention can be used to treat bacterial Gram-positive, Gram-negative and anaerobic infections, especially infections caused by resistant Gram-positive organism and Gram-negative organism, mycobacterial infections and emerging nosocomial pathogen infections.

18 Claims, No Drawings

US 7,868,173 B2

PRODRUGS OF BENZOQUINOLIZINE-2-CARBOXYLIC ACID

CROSS REFERENCE TO RELATED APPLICATIONS

This application is a continuation-in-part of U.S. patent application Ser. No. 11/430,017 filed May 9, 2006 now abandonded, which claims the benefit of Indian application No. 321/MUM/2006, filed on Mar. 7, 2006. The entire disclosures of the prior applications are hereby incorporated by reference.

STATEMENT REGARDING FEDERALLY SPONSORED RESEARCH OR DEVELOPMENT

This invention has been created without the sponsorship or funding of any federally sponsored research or development program.

SEQUENCE LISTING OR PROGRAM

Not Applicable.

BACKGROUND OF THE INVENTION

1. Field of Invention

The instant invention relates to novel prodrugs of optically pure benzoquinolizine-2-carboxylic acid and pharmaceutical compositions that include the prodrugs. The compounds and compositions of the invention can be used to treat bacterial Gram-positive, Gram-negative and anaerobic infections, especially infections caused by resistant Gram-positive organism and Gram-negative organism, mycobacterial infections and emerging nosocomial pathogen infections.

2. Background of the Invention

Prodrugs are therapeutic agents, which are inactive per se but in vivo they are transformed into therapeutically active parent molecule. Prodrugs provide optimal physicochemical, pharmacokinetic and pharmacodynamic properties. They can be designed to overcome pharmaceutical, pharmacokinetic or pharmacodynamic barriers such as insufficient oral absorption, poor solubility, insufficient chemical stability, unacceptable taste or odor, irritation or pain, inadequate blood-brain barrier permeability, toxicity and marked presystemic metabolism.

For patient convenience most drugs are administered by the oral route. There are significant hurdles confronting the delivery of a drug from the oral route, which often means that all the administered compound does not reach its intended site of action. The extent to which the compound can overcome the hurdles to oral drug delivery and reach the systemic circulation is quantified by the term oral bioavailability.

The chiral fluoroquinolone S-(−)-9-fluoro-6,7-dihydro-8-(4-hydroxypiperidin-1-yl)-5-methyl-1-oxo-1H,5H-benzo[i,j]quinolizine-2-carboxylic acid also known as S-(−)-nadifloxacin is described in Japanese patents JP 63,192,753A and JP 05,339,238A. S-(−)-9-fluoro-6,7-dihydro-8-(4-hydroxypiperidin-1-yl)-5-methyl-1-oxo-1H,5H-benzo[i,j]quinolizine-2-carboxylic acid has the potential to be useful as a commercial antibacterial agent, due to its antibacterial activity profile. However S-(−)-9-fluoro-6,7-dihydro-8-(4-hydroxypiperidin-1-yl)-5-methyl-1-oxo-1H,5H-benzo[i,j]quinolizine-2-carboxylic acid sodium salt has a high propensity to cause phlebitis in rats by intravenous route. Also S-(−)-9-fluoro-6,7-dihydro-8-(4-hydroxypiperidin-1-yl)-5-methyl-1-oxo-1H,5H-benzo[i,j]quinolizine-2-carboxylic acid has an aqueous solubility of 0.8-2.0 mg/ml over the pH range 8.0-9.5 at 28° C., thus creating problems in having to formulate the drug as a tablet or capsule, or in making formulations for gavage and parenteral injection. Thus, a suitable entity, which can overcome the above mentioned problems can help in development of a dosage form acceptable for systemic use in humans and animals.

In this direction we have shown that S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt is a broad-spectrum antibiotic, which possesses lower propensity to cause phlebitis in rats by intravenous route as disclosed in PCT application WO 00/68229. The most stable salt form, S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate, is disclosed in PCT application WO 05/023805A1 (and in corresponding U.S. Pat. No. 7,164,023). It is useful to prepare stable pharmaceutical dosage forms, including an aqueous solution. The injectable form is specially suitable for long-term intravenous therapy for treating diseases caused by bacterial infections in view of its favorable aqueous solubility at pH 9.5, its ideal suitability in not causing venous inflammation on repeated intravenous administration, and its safety profile.

However the oral bioavailability of the S-(−)-9-fluoro-6,7-dihydro-8-(4-hydroxypiperidin-1-yl)-5-methyl-1-oxo-1H,5H-benzo[i,j]quinolizine-2-carboxylic acid and S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate has been found to be poor in animals. The poor oral bioavailability of S-(−)-9-fluoro-6,7-dihydro-8-(4-hydroxypiperidin-1-yl)-5-methyl-1-oxo-1H,5H-benzo[i,j]quinolizine-2-carboxylic acid is probably due to the inadequate solubility and hence poor in vivo absorption. Whereas poor oral bioavailability of the L-arginine salt of S-(−)-9-fluoro-6,7-dihydro-8-(4-hydroxypiperidin-1-yl)-5-methyl-1-oxo-1H,5H-benzo[i,j]quinolizine-2-carboxylic acid is probably due to the propensity of the compound to precipitate in the acidic pH while transiting through the gastric region where the pH is ~1 to 2.

Thus, prodrugs approach was envisaged to improve the oral bioavailability of S-(−)-9-fluoro-6,7-dihydro-8-(4-hydroxypiperidin-1-yl)-5-methyl-1-oxo-1H,5H-benzo[i,j]quinolizine-2-carboxylic acid. Prodrugs of S-(−)-9-fluoro-6,7-dihydro-8-(4-hydroxypiperidin-1-yl)-5-methyl-1-oxo-1H,5H-benzo[i,j]quinolizine-2-carboxylic acid are disclosed in our U.S. Pat. No. 6,750,224. The '224 patent discloses two types of prodrugs—the prodrugs at the 2-carboxylic acid and at the 4-hydroxy of the piperidine side chain. The prodrugs disclosed at 4-hydroxy piperidine include amino acid prodrugs. These prodrugs were studied with the aim to develop an oral pharmaceutical composition. The prodrugs of S-(−)-9-fluoro-6,7-dihydro-8-(4-hydroxypiperidin-1-yl)-5-methyl-1-oxo-1H,5H-benzo[i,j]quinolizine-2-carboxylic acid disclosed therein either did not possess optimal features such as adequate solubility across wide pH range which is likely to be present in the alimentary canal, to show substantial prodrug effect or the prodrugs failed to improve oral bioavailability of S-(−)-9-fluoro-6,7-dihydro-8-(4-hydroxypiperidin-1-yl)-5-methyl-1-oxo-1H,5H-benzo[i,j]quinolizine-2-carboxylic acid as compared to S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate. Amongst the amino acid prodrugs, the L-alanine and L-valine prodrugs were also disclosed. Both the prodrugs, possessed limited water solubility (<10 mg/ml). It is generally suggested that inadequate aqueous solubility is an important factor limiting oral bioavailability.

An objective of the present invention is to provide a compound with improved aqueous solubility across a wide pH range with enhanced oral bioavailability, which is likely to be encountered in the alimentary canal.

SUMMARY OF THE INVENTION

The present invention describe the salts of the prodrugs of S-(−)-9-fluoro-6,7-dihydro-8-(4-hydroxypiperidin-1-yl)-5-methyl-1-oxo-1H,5H-benzo[i,j]quinolizine-2-carboxylic acid, of Formula I, Formula I

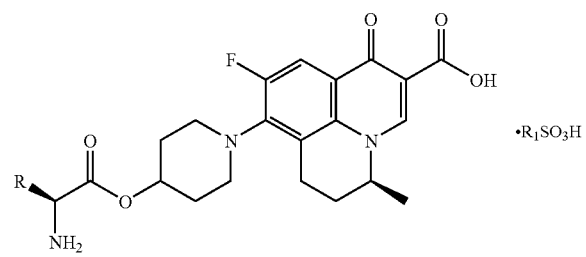

and their pharmaceutically acceptable solvates, polymorphs or hydrates, wherein:

R is $CH_3$ or $CH(CH_3)_2$; and $R_1$ is $C_1$-$C_6$ alkyl or phenyl optionally substituted by one or more substituents selected from $C_1$-$C_6$ alkyl, halogen, nitro, hydroxy or $C_1$-$C_6$ alkoxy.

The present invention also relates to a method of preparation of compound of formula I including the steps of coupling an amine protected L-alanine or L-valine with S-(−)-9-fluoro-6,7-dihydro-8-(4-hydroxypiperidin-1-yl)-5-methyl-1-oxo-1H,5H-benzo[i,j]quinolizine-2-carboxylic acid to form compound of formula II, deprotecting compound of formula and isolating the compound of invention of formula I or a pharmaceutically acceptable salt thereof.

Additionally, this invention provides a process or processes for preparing the compounds of invention of formula I and their polymorphs and hydrates.

The invention also relates to pharmaceutical compositions containing the compounds of invention and to the method for treating or preventing bacterial infections using the compounds and compositions of the invention.

The details of one or more embodiments of the invention are set forth in the description below. Other features, objects and advantages of the invention will be apparent from the description and claims.

DETAILED DESCRIPTION OF THE INVENTION

The present invention describe prodrugs of S-(−)-9-fluoro-6,7-dihydro-8-(4-hydroxypiperidin-1-yl)-5-methyl-1-oxo-1H,5H-benzo[i,j]quinolizine-2-carboxylic acid, of Formula I Formula I

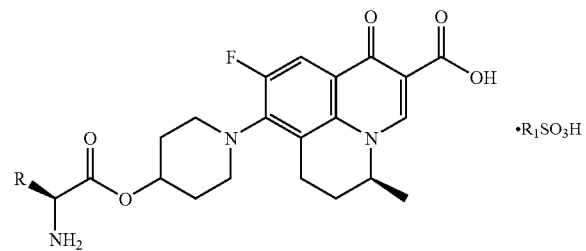

and their pharmaceutically acceptable solvates, polymorphs or hydrates, wherein:

R is $CH_3$ or $CH(CH_3)_2$; and $R_1$ is $C_1$-$C_6$ alkyl or phenyl optionally substituted by one or more substituents selected from $C_1$-$C_6$ alkyl, halogen, nitro, hydroxy or $C_1$-$C_6$ alkoxy.

Aqueous solubility is an important parameter for the oral bioavailability of a drug. Aqueous solubility of the compounds of the invention was found to be >200 mg/ml at pH 7 which is substantially greater than the free base or the hydrochloride salt.

The compounds of formula I have shown to provide particularly good absorption reflected in the increased AUC and $C_{max}$ by oral route in rats as compared to the parent compound i.e. S-(−)-9-fluoro-6,7-dihydro-8-(4-hydroxypiperidin-1-yl)-5-methyl-1-oxo-1H,5H-benzo[i,j]quinolizine-2-carboxylic acid and its L-arginine salt. Also as compared to the hydrochloride salt of the prodrug, S-(−)-9-fluoro-6,7-dihydro-8-(4-L-alaninyloxypiperidin-1-yl)-5-methyl-1-oxo-1H,5H-benzo[i,j]quinolizine-2-carboxylic acid, the compounds of invention showed increased AUC and $C_{max}$ by oral route in rats. Furthermore, the lower solubility of hydrochloride salt of S-(−)-9-fluoro-6,7-dihydro-8-(4-L -alaninyloxypiperidin-1-yl)-5-methyl-1-oxo-1H,5H-benzo[i,j]-quinolizine-2-carboxylic acid may suffer from common ion effect while passing through the gastric region. Also the compounds of invention of formula I have been found to be well tolerated at high doses in rodents and dogs.

Another embodiment of the present invention provides a method for preparation of the compounds of formula I. The compounds of formula I can be prepared by coupling of the amine protected amino acid, with S-(−)-9-fluoro-6,7-dihydro-8-(4-hydroxypiperidin-1-yl)-5-methyl-1-oxo-1H,5H-benzo[i,j]quinolizine-2-carboxylic acid in the presence of a coupling agent. The amino acid used is L-alanine or L-valine. The compound of formula II is deprotected to afford the compound of invention of formula I.

The compounds of invention can be prepared from S-(−)-9-fluoro-6,7-dihydro-8-(4-hydroxypiperidin-1-yl)-5-methyl-1-oxo-1H,5H-benzo[i,j]quinolizine-2-carboxylic acid by esterifying the 4-hydroxy-piperidine with N-tert-butoxycarbonyl-L-alanine or N-tert -butoxycarbonyl-L-valine in presence of a coupling agent by using the techniques known in the art. Typically the coupling reaction is performed in the presence of a coupling agent in a suitable solvent and in presence of a one or more base at a temperature ranging between −30° C. to +150° C. to give the compound of formula II. Preferred coupling agents include carbodiimides, 2,4,6-trichlorobenzoyl chloride, methanesulfonyl chloride and the like. The cabodiimides such as dicyclohexylcarbodiimide or N-(3-dimethylaminopropyl)-N-ethyl carbodiimide can be used as coupling agents. The suitable solvent is selected from halogenated solvents such as dichloromethane, chloroform, or dipolar aprotic solvents such as tetrahydrofuran, N,N-dimethylformamide or mixtures thereof. One or more base is selected from triethylamine, N,N-dimethylaminopyridine, Hunig's base (N,N-diisopropylethylamine).

The coupling reaction is performed by treating S-(−)-9-fluoro-6,7-dihydro-8-(4-hydroxypiperidin-1-yl)-5-methyl-1-oxo-1H,5H-benzo[i,j]quinolizine-2-carboxylic acid with N-tert-butoxycarbonyl-L-alanine or N-tert-butoxycarbonyl-L-valine in halogenated hydrocarbon such as dichloromethane, chloroform or ethylene dichloride and in the presence of N,N-dimethylaminopyridine and coupling agent dicyclohexylcarbodiimide at −10 to 0° C. Or alternatively the coupling reaction can be performed by treating S-(−)-9-fluoro-6,7-dihydro-8-(4-hydroxypiperidin-1-yl)-5-methyl-1-oxo-1H,5H-benzo[i,j]quinolizine-2-carboxylic acid with N-tert-butoxycarbonyl-L-alanine or N-tert-butoxycarbonyl-L-valine in tetrahydrofuran and dimethylformamide using the coupling agent trichlorobenzoyl chloride in presence N,N-dimethylaminopyridine at −10 to 0° C. The coupling reaction can also be carried out by treating S-(−)-9-fluoro-6,7-dihydro-8-(4-hydroxypiperidin-1-yl)-5-methyl-1-oxo-1H,5H-benzo[i,j]quinolizine-2-carboxylic acid with N-tert-butoxycarbonyl-L-alanine or N-tert-butoxycarbonyl-L-valine in tetrahydrofuran and dimethylformamide using the methanesulfonyl chloride as the coupling agent in presence of triethylamine at −10 to 0° C.

The deprotection step of the N-tert-butoxycarbonyl (BOC) can be performed by using the methods described in T. W. Greene and P. G. M. Wuts, *Protective groups in organic synthesis,* 3rd edition, John Wiley & Sons, New York (1999). Accordingly, the deprotection can be carried out by treating compound of formula II using mild acidic conditions in aqueous or non-aqueous solutions. The solvents, which can be used, for the deprotection step in solution, aqueous acids with or without addition of organic solvents, or non-aqueous organic solvents. The organic solvents are selected from the group comprising acetone, acetonitrile, ethanol, isopropanol, or mixtures thereof. The acidic conditions can be used by using a mineral acid such as hydrochloric acid or like, alternatively using any other organic acid such as methanesulfonic acid, toluenesulfonic acid, benzenesulfonic acid, p-nitrobenzenesulfonic acid, trifluoroacetic acid, acetic acid, formic acid or mixtures thereof. Preferably, the compound of formula II is treated with methanesulfonic acid, p-touluenesulfonic acid, benzenesulfonic acid, p-bromobenzenesulfonic acid or p-nitrobenzenesulfonic acid at a temperature ranging from −10° C. to 100° C. in acetone or acetonitrile to afford the compound of invention of formula I.

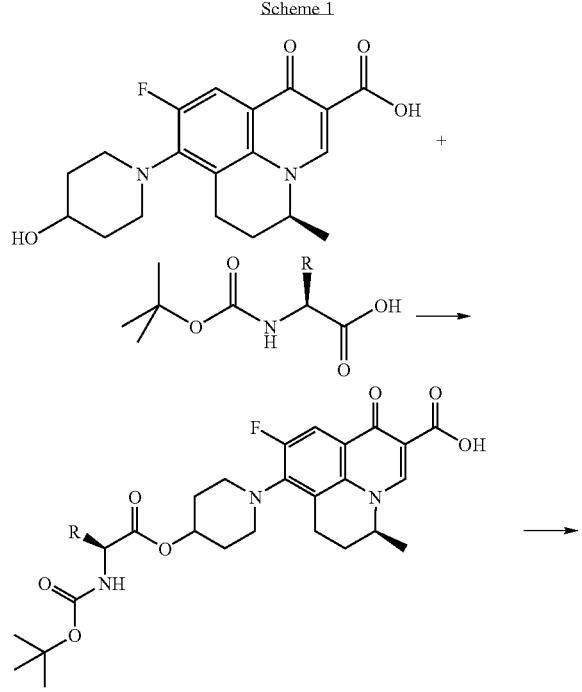

Scheme 1

Formula II

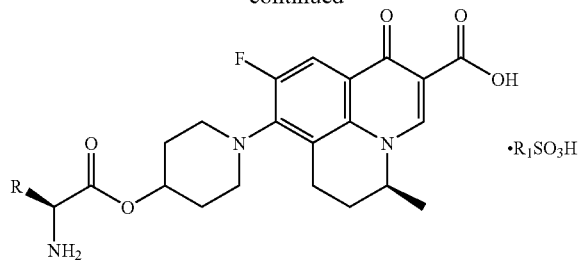

Formula I

Another aspect of the present invention is to purify the crude product of the compound of invention of formula I. The purification of the compounds of invention is done by removal of the impurities by dissolving the impurities in organic solvent. The solvents used are acetone, diethylether or mixtures thereof.

Polymorphs of the compounds of formula I may be prepared by crystallization of the compound of formula I under various conditions, for example, temperature, time and/or use of particular solvents. Hydrates of the compounds of formula I may be prepared by methods known to those of skilled in the art.

The term "$C_1$-$C_6$ alkyl" refers to saturated, straight or branched chain hydrocarbon radicals containing between one and six carbon atoms. Examples of $C_1$-$C_6$ alkyl radicals, include but are not limited to, methyl, ethyl, propyl, butyl, pentyl, hexyl, and their branched isomers such as iso-propyl, iso-butyl, tert-butyl.

The term "$C_1$-$C_6$ alkoxy" refers to an oxygen radical having a hydrocarbon chain substituent, where the hydrocarbon chain is an alkyl (i.e. —O-alkyl). Examples of $C_1$-$C_6$ alkoxy are methoxy, ethoxy, propyloxy, isopropyloxy, butyloxy, pentyloxy, hexyloxy.

The term "halogen" as used herein refers to an atom selected from fluorine, chlorine, bromine and iodine.

The term "nitro" refers to a group of formula —$NO_2$—.

The term "alkyl sulphonic acid" refers to the formula ($C_1$-$C_6$ alkyl) -$SO_3H$; for example methane sulphonic acid ($CH_3SO_3H$), ethane sulphonic acid ($CH_3CH_2SO_3H$).

The invention also relates to liquid and solid pharmaceutical formulations which comprise the prodrug of the invention, such as for example, injectable solutions, suspensions, emulsions, tablets, coated tablets, coated tablet cores, capsules, solutions, troches, dispersions, pellets, granules, suppositories, hard or soft gelatin capsules, and the like.

The pharmaceutical compositions are prepared according to conventional procedures used by persons skilled in the art to make stable and effective compositions. Such methods include by mixing, stirring, suspending, dispersing, emulsifying, dissolving and the like, the active compounds with or in the pharmaceutical auxiliaries such as a carrier, diluent, solvent or excipient and processing the components to pharmaceutically suitable forms for parenteral, oral, intranasal, buccal or rectal administration and the like. In the solid, liquid, parenteral dosage forms, an effective amount of the active compound or the active ingredient is any amount, which produces the desired results. It has been found in accordance with the present invention that the advantageous solubility properties of the prodrug of invention can be applied to the formulation of pharmaceutical dosage forms. It can also be used to prepare tablets by wet granulation; or by conventional dry granulation. It can also be used to prepare aqueous dosage forms.

The dosage forms can be prepared by any conventional techniques recognized in the art, but would preferably be formulated by mixing the prodrug of the invention with the other ingredients. The other ingredients utilized to formulate solid oral dosage forms would include conventional inert ingredients such as microcrystalline cellulose, methyl cellulose and the like, suitable sweetening, coloring and/or flavouring agents, and preservatives thereof if required. Such solid oral dosage forms or dry formulations suitable for the preparation of suspensions would be formulated such that they would contain an effective dose of the compound of the invention. In general, solid dosage forms containing 100 mg-1500 mg of the compound of the invention are contemplated. Preparations suitable for oral suspension would contain a similar dosage.

Pharmaceutical formulations can be formulated together with auxiliaries and additives usually employed in pharmacy, such as tablet binders, fillers, preservatives, tablet disintegrating agents, flow regulating, agents, plasticizers, wetting agents, dispersing agents, emulsifiers, solvents, pH altering additives, flavourings and the like. A second preferred method is parenterally for intramuscular, intravenous or subcutaneous administration.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent. It is preferred that the concentration of active ingredient in the injectable preparation be in the range of 0.1 mg/ml to 100 mg/ml.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

The total daily dose range is generally from about 200 mg to about 5000 mg of the prodrug of invention. Preferably, the total daily dose range of 300 mg to 3000 mg of the prodrug of invention. However, the dose may be higher or lower depending on the needs and conditions of the patient.

The antibacterial compounds and the pharmaceutical compositions of the invention are useful in the treatment of humans and animals having a broad spectrum of bacterial infections such as impetigo, pneumonia, bronchitis, pharyngitis, endocarditis, urinary tract infections, diabetes foot ulcers, gastro-intestinal infections and bacteremia. These bacterial infections could be caused by any of the following bacteria—*Staphylococcus aureus*, coagulase negative staphylococci, methicillin-resitant *Staphylococcus aureus*, methicillin-resitant coagulase negative staphylococci, enterococci, beta-haemolytic streptococci, viridans group of streptococci, mycobacterial infections due to multi-drug resistant *M. tuberculosis* and other atypical mycobacteria such as *M. intracellulare* and *M. avium*, as well as newly emerging Gram-negative pathogens such as *Chryseobacterium meningosepticum*, *Chryseobacterium indologense* and other Gram-negative pathogens such as *E. coli*, *Klebsiella*, *Proteus*, *Serratia*, *Citrobacter*, and *Pseudomonas*.

The present invention also encompasses an anti infective composition for the treatment of humans and animals in need of prophylaxis and/or therapy for systemic infections especially resistant gram-positive organism infections, gram-negative organism infections, mycobacterial infections and nosocomial pathogen infections, which composition comprises an amount of the compound of the invention substantially sufficient to eradicate said infection, but not to cause any undue side effects. The compound and compositions of this invention can be administered to humans and animals who are at risk of being infected, for example a compound or composition of this invention can be administered to a patient prior to and/or after surgery, health care workers or others who are at risk of being infected.

The present invention encompasses administering the compounds to a human or animal subject. The compound and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio. The animals which can be treated by using compounds of the invention include, but are not limited to, mammals, fishes, birds.

The following detailed examples serve to more fully illustrate the invention without limiting its scope. It is understood that various other embodiments and modifications in the practice of the invention will be apparent to, and can be readily made by, those ordinary skill in the art without departing from the scope and spirit of the invention as described above. Accordingly, it is not intended that the scope of the claims appended hereto be limited to the exact description set forth above, but rather than the claims be construed as encompassing all of the features of patentable novelty that reside in the present invention, including all of the features and embodiments that would be treated as equivalents thereof by those skilled in the relevant art. The invention is further described with reference to the following experimental work.

The following detailed examples serve to more fully illustrate the invention without limiting its scope.

Experimental:
(S)-9-Fluoro-6,7-dihydro-8-(4-hydroxypiperidin-1-yl)-5-methyl-1-oxo-1H,5H-benzo[i,j]quinolizine-2-carboxylic acid was prepared as per procedure described in *Chem. Pharm. Bull.* 1996, 44(4), 642-645.

EXAMPLE-1

Preparation of (2'S,5S)-9-fluoro-6,7-dihydro-8-(4-(N-tert-butoxycarbonyl-L-alaninyl-oxy)-piperidin-1-yl)-5-methyl-1-oxo-1H,5H-benzo[i,j]quinolizine-2-carboxylic acid Method-1: To a mixture of N-tert-butoxycarbonyl-L-alanine (473 g) in dichloromethane (2 L), dicyclohexylcarbodiimide (515 g) dissolved in dichloromethane (2 L) was charged at −10 to 0° C. to provide a turbid suspension. To the turbid suspension, 300 g of (S) -9-fluoro-6,7-dihydro-8-(4-hydroxy-piperidin-1-yl)-5-methyl-1-oxo-1H,5H-benzo[i,j] quinolizine-2-carboxylic acid was added followed by 4-N,N-dimethylamino pyridine (58 g) and the reaction mixture was stirred at −10 to 5° C. temperature over a period of 2 h. Suspension was filtered and solid was washed with 500 ml of dichloromethane. The filtrate was washed with water. Filtrate was dried over anhydrous sodium sulfate. Dried organic layer was then concentrated to its half volume where upon solid was precipitated. The solid was filtered and washed with 300 ml of dichloromethane. Clear organic filtrate was concentrated to dryness to provided an oily mass. Oily mass was triturated with diethyl ether (4 L) to provide white solid. The solid was filtered under suction and washed with diethyl ether (1 L) to provide title compound in 415 g (94%) quantity.

Method-2: To a mixture of triethylamine (98.0 ml) and N-tert-butoxycarbonyl-L -alanine (110 g) in tetrahydrofuran (1050 ml) and N,N-dimethyl formamide (350 ml) mixture, was added 2,4,6-trichlorobenzoyl chloride (100 ml). The resultant mixture was stirred at a temperature −5 to 0° C. for 5 h. To the reaction mixture 4-N,N -dimethylamino pyridine (24 g) and (S)-9-fluoro-6,7-dihydro-8-(4-hydroxy-piperidin-1-yl)-5-methyl-1-oxo-1H,5H-benzo[i,j]quinolizine-2-carboxylic acid (70 g) was added. The reaction mixture was stirred for additional 7 h at −5 to 0° C. temperature. The suspension was filtered at room temperature and the filtrate was extracted with ethyl acetate after addition of water. The evaporation of organic layer under reduced pressure provided a sticky solid, which upon triturating with diethyl ether provided a white solid in 85 g quantity.

Method-3: To a solution N-tert-butoxycarbonyl-L-alanine (7.9 g) in tetrahydrofuran (75 ml) and N,N-dimethyl formamide (25 ml) mixture at −10 to 0° C. was added methanesulfonyl chloride (2.42 ml) dropwise. To the above solution triethylamine (8.7 ml) was added dropwise over 5 min. the reaction was stirred for 1.5 h maintaining the temperature between at −10 to 0° C. To the reaction mixture (S)-9-fluoro-6,7-dihydro -8-(4-hydroxy-piperidin-1-yl)-5-methyl-1-oxo-1H,5H-benzo[i,j]quinolizine-2-carboxylic acid (5.01 g) and 4-N,N-dimethylamino pyridine (1.70 g) was added. The reaction mixture was stirred for additional 1 h at −5 to 0° C. temperature. The suspension was filtered at room temperature and the filtrate was diluted with water (300 ml) and extracted with ethyl acetate (150 ml×2). The evaporation of organic layer under reduced pressure provided a sticky solid, which upon triturating with diethyl ether provided a white solid in 6.38 g (86%) quantity.

EXAMPLE-2

Preparation of (2'S,5S)-9-fluoro-6,7-dihydro-8-(4-L-alaninyl-oxy-piperidin-1-yl)-5-methyl-1-oxo-1H, 5H-benzo[i,j]quinolizine-2-carboxylic acid methanesulfonic acid salt To a mixture of (2'S,5S)-9-fluoro-6,7-dihydro-8-(4-N-tert-butoxycarbonyl-L-alaninyloxy-piperidin-1-yl)-5-methyl-1-oxo-1H,5H-benzo[i,j]quinolizine-2-carboxylic acid (415 g) in acetone (4.5 L) was charged methanesulfonic acid (66 ml). Reaction mixture was stirred at 65-67° C. temperature for overnight. The suspension was filtered at 40-45° C. Solid was washed with acetone (1.5 L) followed by diethyl ether (1.5 L). Off white solid was dried under 40 to 45 mm vacuum at 55-60° C. temperature over the period of 3-4 h. Title compound was obtained as a free flowing off white material 383.0 g (93%).

For MF: $C_{23}H_{30}FN_3O_8S$, MS (ES+) m/z 432 (obtained as free base for MF: $C_{22}H_{26}FN_3O_5$); M.P. 278.50° C. by DSC.

EXAMPLE-3

Preparation of (2'S,5S)-9-fluoro-6,7-dihydro-8-(4-L-valinyloxy-piperidin-1-yl)-5-methyl-1-oxo-1H,5H-benzo[i,j]quinolizine-2-carboxylic acid methanesulfonic acid salt Step-1: Preparation of (2'S,5S)-9-fluoro-6,7-dihydro-8-{4-[N-tert-butyloxycarbonyl-L-valinyloxy]-piperidin-1-yl}-5-methyl-1-oxo-1H,5H-benzo[i,j]quinolizine-2-carboxylic acid To a mixture of triethyl amine (14 ml) and N-tert-butyloxycarbonyl-L-valine (18 g) in tetrahydrofuran (50 ml) and N,N-dimethyl formamide (15 ml) mixture, was added 2,4,6-trichlorobenzoyl chloride (14.3 ml). The resultant mixture was stirred at a temperature −5 to 0° C. for 5 h. To the reaction mixture 4-N,N-dimethylamino pyridine (3.4 g) and (S)-9-fluoro-6,7-dihydro-8-{4-hydroxy-piperidin-1-yl}-5-methyl-1-oxo-1H,5H -benzo[i,j]quinolizine-2-carboxylic acid (10 g) was added. The reaction mixture was stirred for additional 7 h at −5 to 0° C. temperature. The suspension was filtered at room temperature and the filtrate was extracted with ethyl acetate after addition of water. The evaporation of organic layer under reduced pressure provided a sticky solid which upon triturating with diethyl ether provided a white solid in 12.5 g quantity.

Step-2: Preparation of (2'S,5S)-9-fluoro-6,7-dihydro-8-{4-L-valinyloxy-piperidin-1-yl}-5-methyl-1-oxo-1H,5H-benzo[i,j]quinolizine-2-carboxylic acid methanesulfonic acid salt A mixture of compound obtained in step-1 (12 g) and methane sulfonic acid (1.81 ml) in acetone (150 ml) was stirred at a temperature 63-65° C. for 10 h. The suspension was filtered at room temperature and solid was washed with acetone to provide off white solid in 9.8 g quantity.

EXAMPLE-4

Preparation of (2'S,5S)-9-fluoro-6,7-dihydro-8-{4-(L-alaninyloxy)-piperidin-1-yl}-5-methyl-1-oxo-1H, 5H-benzo[i,j]quinolizine-2-carboxylic acid toluenesulfonic acid salt To a mixture of (2'S,5S)-9-fluoro-6,7-dihydro-8-(4-N-tert-butoxycarbonyl-L-alaninyloxy-piperidin-1-yl)-5-methyl-1-oxo-1H,5H-benzo[i,j]quinolizine-2-carboxylic acid (3.0 gm; 5.64 mol) in acetone (35 ml) was charged p-toluenesulfonic acid monohydrate (1.61 gm; 8.47 mol). Reaction mixture was refluxed for overnight. The suspension was filtered at 40-45° C. and the solid obtained was washed with acetone followed by diethyl ether. The solid was dried under 40 to 45 mm vacuum at 55-60° C. temperature over the period of 3-4 h to give the title compound as a off white color solid in 3.0 gm (88.23% yield). For MF: $C_{29}H_{34}FN_3O_8S$, MS (M+H) m/z 432 (obtained as free base for MF: $C_{22}H_{26}FN_3O_5$); M.P. 232° C.

EXAMPLE-5

Preparation of (2'S,5S)-9-fluoro-6,7-dihydro-8-{4-(L-alaninyloxy)-piperidin-1-yl}-5-methyl-1-oxo-1H, 5H-benzo[i,j]quinolizine-2-carboxylic acid benzenesulfonic acid salt To a mixture of (2'S,5S)-9-fluoro-6,7-dihydro-8-(4-N-tert-butoxycarbonyl-L-alaninyloxy-piperidin-1-yl)-5-methyl-1-oxo-1H,5H-benzo[i,j]quinolizine-2-carboxylic acid (3.0 gm; 5.64 mol) in acetone (35 ml) was charged benzenesulfonic acid (1.33 gm; 8.41 mol). Reaction mixture was refluxed for overnight. The suspension was filtered at 40-45° C. and the solid obtained was washed with acetone followed by diethyl ether. The solid was dried under 40 to 45 mm vacuum at 55-60° C. temperature over the period of 3-4 h to give the title compound as a pale yellow color solid in 3.1 gm (90.0% yield). For MF: $C_{28}H_{32}FN_3O_8S$, MS (M+H) m/z 432 (obtained as free base for MF: $C_{22}H_{26}FN_3O_5$); M.P. 229° C.

EXAMPLE-6

Preparation of (2'S,5S)-9-fluoro-6,7-dihydro-8-{4-(L-alaninyloxy)-piperidin-1-yl}-5-methyl-1-oxo-1H,5H-benzo[i,j]quinolizine-2-carboxylic acid nitrobenzenesulfonic acid salt To a mixture of (2'S,5S)-9-fluoro-6,7-dihydro-8-(4-N-tert-butoxycarbonyl-L-alaninyloxy-piperidin-1-yl)-5-methyl-1-oxo-1H,5H-benzo[i,j]quinolizine-2-carboxylic acid (3.0 gm; 5.64 mol) in acetone (35 ml) was charged p-nitrobeznenesulfonic acid (1.73 gm; 8.47 mol). Reaction mixture was refluxed for overnight. The suspension was filtered at 40-45° C. and the solid obtained was washed with acetone followed by diethyl ether. The solid was dried under 40 to 45 mm vacuum at 55-60° C. temperature over the period of 3-4 h to give the title compound as a pale yellow color solid in 3.3 gm (92.43% yield). For MF: $C_{28}H_{31}FN_4O_{10}S$, MS (M+H) m/z 432 (obtained as free base for MF: $C_{22}H_{26}FN_3O_5$); M.P. 240° C.

TEST EXAMPLE-1

Solubility analysis: Method for determining aqueous solubility at different physiological pH at 25-30° C. temperature: To accurately weighed amount of test substance, particular buffer solution was added in portion (about 50 microliter portions) at 25-30° C. temperature till solid is completely dissolved and clear solution is obtained.

TABLE 1

Solubilty at pH 7

| Compound | Solubility (mg/ml) at pH 7 |
|---|---|
| (5S)-9-fluoro-6,7-dihydro-8-(4-hydroxy-piperidin-1-yl)-5-methyl-1-oxo-1H,5H-benzo[i,j]quinolizine-2-carboxylic acid | <1 |
| (5S)-9-fluoro-6,7-dihydro-8-(4-hydroxy-piperidin-1-yl)-5-methyl-1-oxo-1H,5H-benzo[i,j]quinolizine-2-carboxylic acid L-arginine salt tetrahydrate | <1 |
| (2'S,5S)-9-fluoro-6,7-dihydro-8-(4-L-alaninyloxy-piperidin-1-yl)-5-methyl-1-oxo-1H,5H-benzo[i,j]quinolizine-2-carboxylic acid hydrochloride salt | 4 |
| (2'S,5S)-9-fluoro-6,7-dihydro-8-(4-L-valinyloxy-piperidin-1-yl)-5-methyl-1-oxo-1H,5H-benzo[i,j]quinolizine-2-carboxylic acid | <1 |
| (2'S,5S)-9-fluoro-6,7-dihydro-8-(4-L-alaninyloxy-piperidin-1-yl)-5-methyl-1-oxo-1H,5H-benzo[i,j]quinolizine-2-carboxylic acid methanesulfonic acid salt | >200 |
| (2'S,5S)-9-fluoro-6,7-dihydro-8-(4-L-valinyloxy-piperidin-1-yl)-5-methyl-1-oxo-1H,5H-benzo[i,j]quinolizine-2-carboxylic acid methanesulfonic acid salt | >200 |

BIOLOGICAL EXAMPLE

Method for pharmacokinetic (PK) study in Sprague Dawley rats: Pharmacokinetic study was conducted on male Sprague Dawley rats weighing 200-220 g fasted overnight. (2'S,5S)-9-fluoro-6,7-dihydro-8-(4-L-alaninyloxy-piperidin-1-yl)-5-methyl-1-oxo-1H,5H-benzo[i,j]-quinolizine-2-carboxylic acid methanesulfonic acid salt (A), (2'S,5S)-9-fluoro-6,7-dihydro-8-(4-L-alaninyloxy-piperidin-1-yl)-5-methyl-1-oxo-1H,5H-benzo[i,j]quinolizine-2-carboxylic acid hydrochloride salt (B) and (2'S,5S)-9-fluoro-6,7-dihydro-8-(4-L-valinyloxy-piperidin-1-yl)-5-methyl-1-oxo-1H,5H-benzo[i,j]quinolizine-2-carboxylic acid methanesulfonic acid salt (C) were dissolved in Milli Q water. Compounds A, B and C were administered at the dose of 50 mg/kg orally calculated on the basis of active ingredient. (5S)-9-fluoro-6,7-dihydro-8-(4-hydroxy-piperidin-1-yl)-5-methyl-1-oxo-1H,5H-benzo[i,j]quinolizine-2-carboxylic acid L-arginine salt (D) was dissolved in 1% Tween prior to use. Compounds A and D were administered at the dose of 200 mg/kg orally calculated on the basis of active ingredient. Dose volume was 0.5 ml/200g. Blood samples were collected at predetermined time intervals i.e. 0, 0.5, 1, 2, 4, 6 & 8 h in eppendorff vials containing 10 µl saturated solution of sodium fluoride. Plasma was collected after centrifugation of blood sample at 10000 rpm for 10 min. Plasma samples were analyzed on HPLC for determining drug levels. PK parameters AUC, $C_{max}$ were calculated by non-compartmental analysis by using Winnonlin software.

TABLE 2

% Improvement of $C_{max}$ and AUC in rat study by oral dose.

| % Improvement | % Increase in $C_{max}$ | % Increase in AUC |
|---|---|---|
| A as compared to B 50 mg/kg per os dose | 300 | 175 |
| A as compared to D 200 mg/kg per os dose | 200 | 120 |
| C as compared to D 50 mg/kg per os dose | 97 | 92 |

The invention claimed is:

1. Compounds having the structure of Formula I,

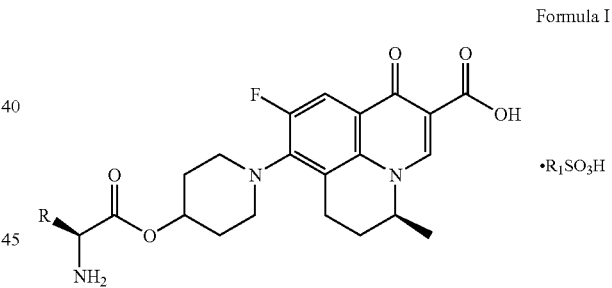

Formula I wherein:
R is $CH_3$ or $CH(CH_3)_2$; and
$R_1$ is $C_1$-$C_6$ alkyl or phenyl optionally substituted by one or more substituents selected from $C_1$-$C_6$ alkyl, halogen, nitro, hydroxy or $C_1$-$C_6$ alkoxy.

2. The compounds according to claim 1, wherein the $R_1$ is $C_1$-$C_6$ alkyl.

3. The compounds according to claim 1, wherein the $R_1$ is a phenyl group optionally substituted by one or more susbtituents selected from $C_1$-$C_6$ alkyl, halogen, nitro, hydroxyl, or $C_1$-$C_6$ alkoxy.

4. The compounds according to claim 1 wherein R is $CH_3$ or $CH(CH_3)_2$ and $R_1$ is methyl, ethyl, phenyl, p-nitrophenyl, tolyl.

5. A process for the preparation of a compound of Formula (I) according to claim 1, the process comprising:
a) coupling S-(-)-9-fluoro-6,7-dihydro-8-(4-hydroxypiperidin-1-yl)-5-methyl-1-oxo-1H,5H-benzo[i,j] quinolizine-2-carboxylic acid with amine protected L-alanine or L-valine in one or more solvents to give protected compound of Formula II;

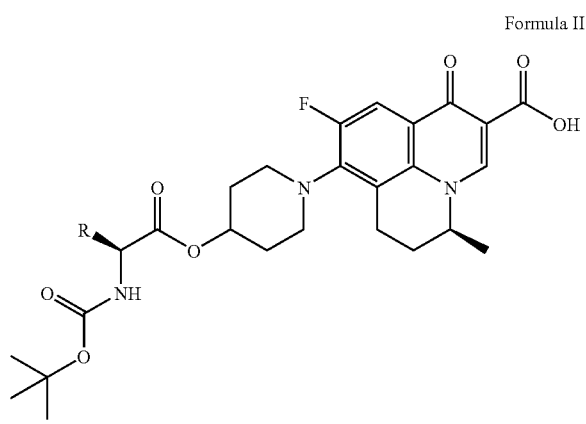

Formula II b) deprotecting the compound of Formula II with a sulfonic acid of the general Formula $R_1$—$SO_3H$, wherein $R_1$ is as defined in claim 1;

c) isolating the compound of Formula I.

6. The process according to claim 5, wherein the coupling reaction is carried out in the presence of a coupling agent.

7. The process according to claim 6, wherein the coupling agent comprises one or more of dicyclocarbodiimide, 2,4,6-trichlorobenzoyl chloride, and methanesulfonyl chloride.

8. The process according to claim 5, further comprising carrying out the coupling reaction in the presence of a base.

9. The process according to claim 8, wherein the base comprises one or more of triethylamine, N,N-dimethylaminopyridine, and diisopropylethylamine.

10. The process according to claim 5, wherein the solvent comprises one or more of dichloromethane, chloroform, ethylene dichloride, tetrahydrofuran, N,N-dimethylformamide, and mixtures thereof.

11. The process according to claim 5, wherein the coupling reaction is performed at a temperature from about −10° C. to about 0 ° C.

12. The process according to claim 5, wherein the sulfonic acid used is alkyl sulphonic acid.

13. The process according to claim 12, wherein the sulfonic acid is methane sulphonic acid.

14. A pharmaceutical composition comprising a therapeutically effective amount of one or more compounds as defined in claim 1 together with pharmaceutically acceptable carriers, excipients or diluents.

15. A method of treating or preventing a bacterial infections in a mammal in need of such treatment comprising administering to the said therapeutically effective amount of one or more compounds of claim 1.

16. The method of claim 15, wherein the bacterial infection is impetigo, pneumonia, bronchitis, pharyngitis, endocarditis, urinary tract infections, diabetes foot ulcers, gastro-intestinal infections or bacteremia.

17. The method of claim 15, wherein the bacterial infection is caused by Gram-positive, Gram-negative or anaerobic bacteria.

18. The method of claim 17, wherein the Gram-positive, Gram-negative or anaerobic bacteria is selected from *Staphylococcus aureus*, coagulase negative staphylococci, methicillin-resitant *Staphylococcus aureus*, methicillin-resitant coagulase negative staphylococci, enterococci, beta-haemolytic streptococci, viridans group of streptococci, mycobacterial infections due to multi-drug resistant *M. tuberculosis* and other atypical mycobacteria such as *M. intracellulare* and *M. avium*, as well as newly emerging Gram-negative pathogens such as *Chryseobacterium meningosepticum*, *Chryseobacterium indologense* and other Gram-negative pathogens such as *E. coli*, Klebsiella, Proteus, Serratia, Citrobacter, and Pseudomonas.

* * * * *